(12) United States Patent
Lai et al.

(10) Patent No.: US 8,915,594 B2
(45) Date of Patent: Dec. 23, 2014

(54) REFRACTION SYSTEM FOR FACILITATING CONTACT LENS FITTING

(71) Applicants: Ming Lai, Dublin, CA (US); Meijuan Yuan, Dublin, CA (US)

(72) Inventors: Ming Lai, Dublin, CA (US); Meijuan Yuan, Dublin, CA (US)

(73) Assignee: MD Lasers & Instruments, Inc., Pleasanton, CA (US)

( * ) Notice: Subject to any disclaimer, the term of this patent is extended or adjusted under 35 U.S.C. 154(b) by 229 days.

(21) Appl. No.: 13/669,166

(22) Filed: Nov. 5, 2012

(65) Prior Publication Data

US 2013/0135586 A1  May 30, 2013

Related U.S. Application Data

(60) Provisional application No. 61/629,749, filed on Nov. 25, 2011.

(51) Int. Cl.
  *A61B 3/10*  (2006.01)
  *A61B 3/00*  (2006.01)
  *A61B 3/18*  (2006.01)

(52) U.S. Cl.
  CPC ............... *A61B 3/18* (2013.01); *A61B 3/1015* (2013.01)
  USPC ........................................ 351/216; 351/247

(58) Field of Classification Search
  USPC ........................ 351/205, 216, 219, 246, 247
  See application file for complete search history.

(56) References Cited

U.S. PATENT DOCUMENTS

| | | |
|---|---|---|
| 5,617,157 A | 4/1997 | Shalon et al. |
| 6,382,795 B1 | 5/2002 | Lai |
| 6,406,146 B1 | 6/2002 | Lai |
| 6,575,572 B2 | 6/2003 | Lai et al. |
| 7,425,067 B2 | 9/2008 | Warden et al. |
| 7,909,461 B2 | 3/2011 | Warden et al. |
| 2005/0241653 A1 | 11/2005 | Van Heugten et al. |
| 2005/0243276 A1 | 11/2005 | Van Heugten et al. |

*Primary Examiner* — Jack Dinh (57) ABSTRACT

The present invention contemplates a refraction system facilitating for contact lens fitting via measuring the patient's refraction on the corneal plane and via introducing a conjugated plane of the corneal plane for insertion of a contact lens simulator or phase plate. The present invention also contemplates a refraction system to integrate the objective and subjective measurement into a single instrument. The present invention further contemplates a refraction system with open-field and binocular viewing to overcome instrument myopia and to measure accommodation. The present invention also further contemplates a refraction system employing a pair of optical trombones to eliminate the need of flipping plurality sets of trial lenses for defocus corrections. The present invention even further contemplates a multiple vergence acuity chart to facilitate patient's judgment of best corrected visual acuity. The present invention is thus aimed to provide a refraction system that overcomes the identified issues with the commonly used auto-refractor and phoropter and that enables effective use of contact lens simulators or phase plates to facilitate fitting of multifocal contact lenses for presbyopia correction.

20 Claims, 9 Drawing Sheets

REFRACTION SYSTEM FOR FACILITATING CONTACT LENS FITTING

This application is a continuation in part of U.S. Provisional Application No. 61/629,749, filed on Nov. 25, 2011.

1. RELATED FIELD

The present invention relates to a method and apparatus for measuring refractive errors of a human eye and for facilitating contact lens fitting. In particular, the invention relates to a method and apparatus for measuring refractive errors of a human eye via implementing objective and subjective measurements into a single instrument, and for facilitating contact lens fitting via providing a corneal-conjugated plane for contact lens simulator or phase plate.

2. BACKGROUND

Contact lens fitting is a time consuming and less comfort process. Typically, contact lens fitting involves two major steps: 1) measuring the patient's refraction errors and 2) fitting contact lens for good visual performance and eye comfort. The first step is to place various trial lenses, one by one, in front of the patient's eye and to enable the patient to determine his best corrected visual acuity, which is then written as refraction prescription for eyeglasses or contact lenses. The second step is to put various contact lenses, one at a time, onto the patient's eye and to enable the patient to select the lens with acceptable visual performance and eye comfort. The chances are that the patient may need to go through many lens insertions or even several clinic visits before a pair of acceptable contact lenses can be identified.

Contact lens fitting becomes much more elaborating when to fit multifocal or aspherical contact lenses for presbyopia correction. In addition to every fitting consideration for a conventional contact lens, fitting a multifocal or aspherical contact lens further involves many more parameters and variations, including the added power needed for each eye, the pupil size effect on optical zone selections for added powers, the tolerance of binocular offset in added powers, and the balance between visual acuity for far and near. The chances are that the patient may need to go through too many lenses to try and may decide to give up before a pair of acceptable multifocal lenses is identified.

Auto-refractor and phoropter are commonly used for providing refraction prescription for eyeglass or contact lenses. An auto-refractor is used to produce objective measurement of eye spherical defocus power, cylinder power and cylinder axis. A phoropter is used to refine the measurement of auto-refractor through subjective response from the patients. The auto-refractor and phoropter are each a stand-alone instrument, and they require different sitting and alignment to perform the measurements. Typically it takes 10 to 30 minutes to make a thorough refraction measurement with auto-refractor and phoropter.

An auto-refractor typically measures one eye at a time and directs the subject eye looking at a fixation target inside the instrument. Instrument myopia, due to fixating at an internal target, is commonly an issue to limit measurement accuracy and reliability.

A phoropter is an instrument used to measure refraction status of the eyes. Conventionally, it contains many lenses which are then congaed in front of the eyes while the patient is looking at an eye chart. This is when the doctor usually asks, "which is better, one or two?"

Auto-phoropter is a good advancement from phoropter and is equipped with a control box and motorized mechanism to change trial lenses. Auto-phoropter is basically a motorized phoropter, which employs multiple sets of trial lenses on a plurality of rotational wheels to produce refraction corrections for sphere and astigmatism. The measurement procedure of an auto-phoropter, however, is still elaborating and time consuming.

Besides, a phoropter measures the patient refraction errors referring to a trial lens plane but not on the corneal plane. The nominal distance from the trial lens plane to the corneal plane is typically 12 mm, but the actual distance varies from patient to patient. This actual distance is required to convert accurately the phoropter measurement to prescription for contact lenses, especially for high myopia eyes.

Contact lens simulators or phase plates have been used to evaluate contact lens visual performance without placing a real contact lens on a subject cornea. Contact lens simulators or phase plates are typically made of a thin piece of PMMA and may have similar optical characters of a multifocal or aspherical contact lens when viewing through the lens center. When a contact lens simulator or phase plate is inserted in an eyeglass trial frame, the subject eye may look through the lens center and experience the optical performance of the contact lens in simulation. However, the visual performance test with a contact lens simulator on an eyeglass trail frame is usually less effective, simply because it is placed on an eyeglass plane but not a corneal plane.

3. SUMMARY

The present invention contemplates a refraction system facilitating for contact lens fitting via measuring the patient's refraction on the corneal plane and via introducing a conjugated plane of the corneal plane for insertion of a contact lens simulator or phase plate. The present invention also contemplates a refraction system to integrate the objective and subjective measurement into a single instrument. The present invention further contemplates a refraction system with open-field and binocular viewing to overcome instrument myopia and to measure accommodation. The present invention also further contemplates a refraction system employing a pair of optical trombones to eliminate the need of flipping plurality sets of trial lenses for defocus corrections. The present invention even further contemplates a multiple vergence acuity chart to facilitate patient's judgment of best corrected visual acuity. The present invention is thus aimed to provide a refraction system that overcomes the above identified issues with the commonly used auto-refractor and phoropter and that enables effective use of contact lens simulators or phase plates to facilitate fitting of multifocal contact lenses for presbyopia correction.

Accordingly, a first objective of the present invention is to provide a new and improved refraction system facilitating for contact lens fitting via measuring the patient's refraction on the corneal plane.

A second objective of the present invention is to provide a new and improved refraction system to integrate both objective and subjective measurements into a single instrument.

A third objective of the present invention is to provide a new and improved refraction system with open-field and binocular viewing to overcome instrument myopia and to enable accurate measurement of accommodation.

A fourth objective of the present invention is to provide a new and improved refraction system employing a pair of power-adjustable optical trombones to eliminate the plurality sets of trial lenses for defocus correction.

A fifth objective of the present invention is to provide a new and improved refraction system enabling the insertion of contact lens simulator or phase plate at a corneal conjugated plane to facilitate contact lens fitting for multifocal and aspherical lenses.

A sixth objective of the present invention is to provide a new and improved refraction system providing a multiple vergence acuity chart to facilitate patient's judgment on his best corrected visual acuity.

The above and other objectives and advantages of the present invention will become more apparent in the following drawings, detailed description, and claims.

5. DESCRIPTION

Figure 1:
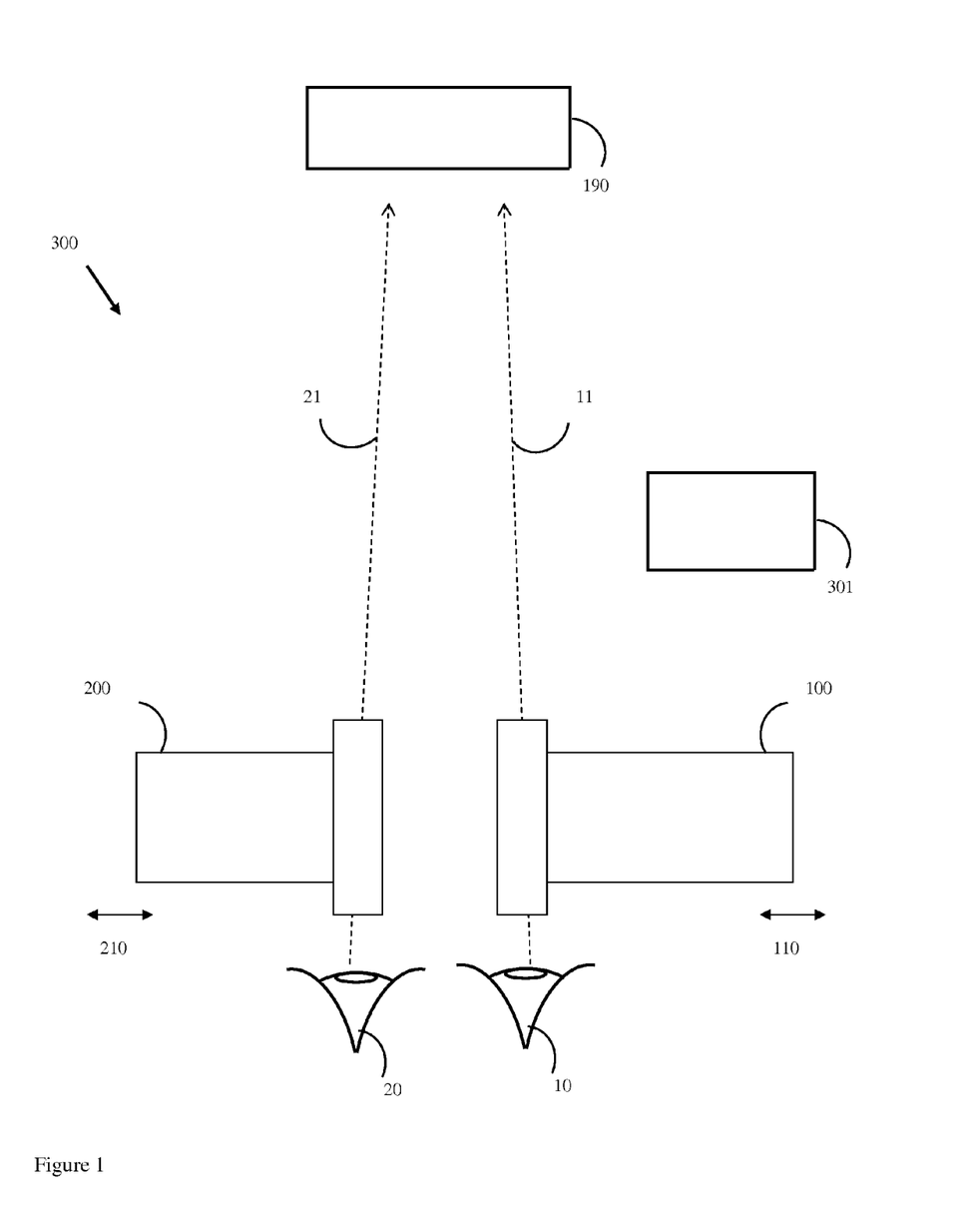
FIG. 1 shows schematically a refraction system comprising a left viewing unit and a right viewing unit and implementing open field and binocular viewing at a multi-vergence acuity chart, in accordance with the present invention.

FIG. 1 shows schematically a refraction system 300 comprising a left viewing unit 200 and a right viewing unit 100 and implementing open field and binocular viewing at a multi-vergence acuity chart 190, in accordance with the present invention. A left subject eye 20 looks through the left viewing unit 200, along viewing path 21, to fixate on the acuity chart 190. A right subject eye 10 looks through the right viewing unit 100, along viewing path 11, to fixate on the same acuity chart 190. Moving mechanism 210 and 110 are to translate the left viewing unit 200 and the right viewing unit 100 to align with pupils of the left eye 20 and the right eye 10. The pupil distance between the left eye 20 and the right eye 10 can thus be measured via separation between the viewing paths 11 and 21, via position readings of the left viewing unit 200 and the right viewing unit 100.

The acuity chart 190 is, in a preferred embodiment, placed outside the refraction system 300 to provide an open view test and to facilitate elimination of instrument myopia. The left viewing unit 200 and the right viewing unit 100 provide independently defocus corrections and have a unit magnification, i.e. the acuity chart 190 appearing the same size and same orientation as seeing with eyeglasses or contact lenses correction. In this application document, a unit magnification refers to a +1 magnification.

In a preferred embodiment, the viewing path 21 appears straight to the left eye 20, and the viewing path 11 appears straight to the right eye 10. The thickness of the viewing unit along the straight viewing path is preferably 100 mm or shorter, such that the viewing experience to the eyes mimics that of a phoropter or auto-phoropter. Such a viewing experience enables near visual acuity test similar to that with a phoropter or auto-phoropter. Such a viewing experience also differentiates the present invention further from various conventional auto-refractors, wavefront aberrometers, and subjective refractors.

The acuity chart 190 is positioned at a predetermined distance from the subject eyes 10 and 20. To be consistent with the convention visual acuity test, the acuity chart 190 is preferably positioned 20 feet (6 meters) away from the eye 10 for distance visual acuity test, and 40 cm away for near visual acuity test.

In a preferred embodiment, the acuity chart 190 is a multiple vergence acuity chart that displays acuity chart with different vergence or distance at different field of view to the subject eyes 10 and 20. For instance, the acuity chart 190 consists of three sections, e.g. the central, the left and the right sections. The three sections may have OD and +/−0.25 D vergence, respectively. (Here D refers to optical diopter thought out this document.) This way, the subject eye 10 can look at the three sections simultaneously and compare the best acuity among the three sections. The best corrected visual acuity shall correspond to a best visual acuity resolvable at the OD section. More details about a multiple vergence acuity chart 190 will be described in a latter section below.

The refraction system 300 also includes a system processor 301, which is coupled electronically to the left viewing unit 200 and the right viewing unit 100 to perform system control, to process measurement data, to calculate prescription for eyeglasses and contact lenses, and to facilitate contact lens fitting. As shown in figures below, the refraction system 300 implements continuous adjustments of defocus power and astigmatism and thus is capable to provide prescription with precision and accuracy higher than the industrial standard of eyeglasses and contact lenses, i.e., 0.25 D in sphere and cylinder power and 1 degree in cylinder axis.

A software algorithm of the system processor 301 is to round off and to convert the initial prescription to precision steps of the industrial standard and to provide this standardized prescription for conventional eyeglasses and contact lenses. In a preferred embodiment, the initial prescription of high precision is provided in a different, non-conventional format for fabricating custom or premium eyeglasses or contact lenses. This initial prescription of high precision can be coded and used for specific lens fabrication process.

Figure 2:
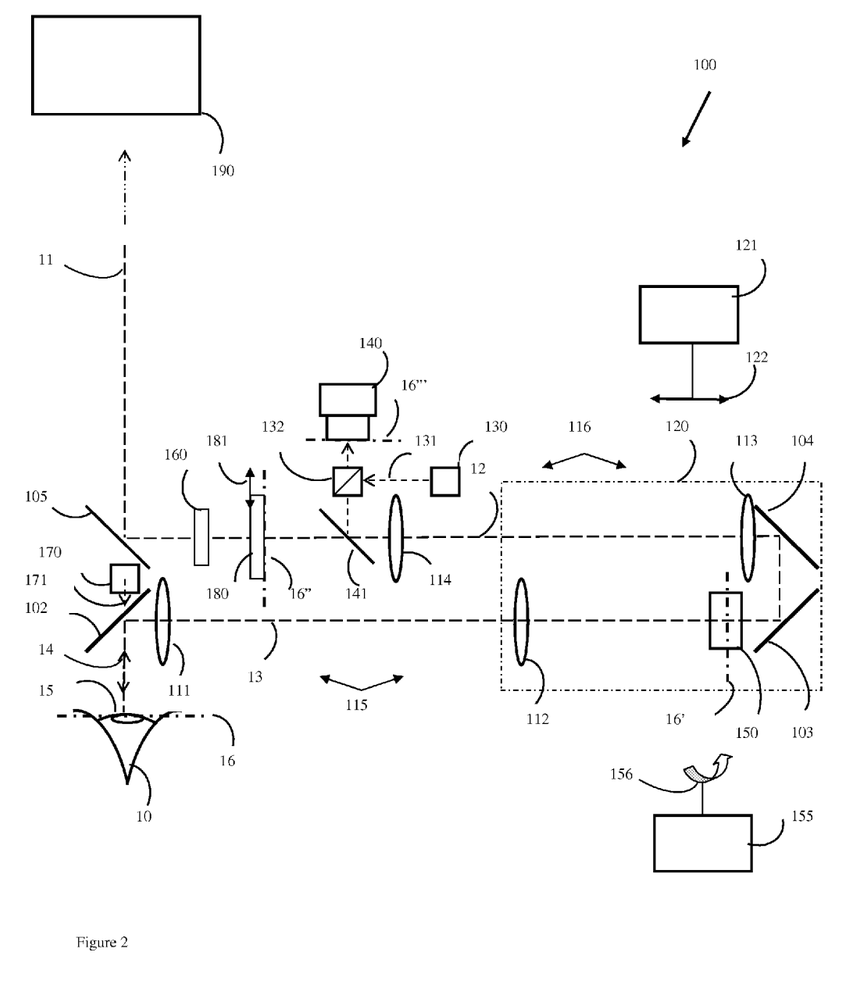
FIG. 2 shows schematically the right viewing unit providing a corneal conjugated plane and enabling insertion of contact lens simulator or phase plate equivalently on a corneal plane, in accordance with the present invention.

FIG. 2 shows schematically the right viewing unit 100 providing a corneal conjugated plane 16" and enabling insertion of contact lens simulator or phase plate 180 equivalently on a corneal plane 16, in accordance with the present invention. The straight viewing path 11 is folded with turning mirrors 102-105. Lenses 111-112 form a first optical trombone 115 and lenses 113-114 forms a second optical trombone 116. Lenses 111-114 are preferably identical, and the pair of optical trombones 115-116 produces a unit magnification, i.e., a magnification of +1. The turning mirrors 103-104 and the lenses 112-113 are mounted on a translation stage 120. A moving mechanism 121 drives the stage 120 moving along direction 122 to change defocus power of the pair of optical trombones 115-116.

The first optical trombone 115 defines a viewing path 13 and a working plane 16, at which the subject cornea 15 is to position. Hence, the working plane 16 is also referred to as the corneal plane 16 in this document. The first optical trombone 115 also defines a first conjugated plane 16' of the working plane 16. In an embodiment of identical lenses 111 and 112, the first trombone 115 has a magnification of −1.

The second optical trombone 116 produces a second conjugated plane 16" of the working plane 16. The second optical trombone 116 also defines a viewing path 12, extending optically from the viewing path 13 to the straight viewing path 11. In an embodiment of identical lenses 113 and 114, the second trombone 116 has also a magnification of −1.

The paired first and second optical trombones 115-116 have collectively a unit magnification of +1. This way, any optics placed at the second conjugated plane 16" appears the same as placed on the cornea plane 16. For instance, a contact lens simulator or phase plate 180 can be inserted, as shown with arrow 181, at the corneal conjugated plane 16". Subject eye 10 looks through the contact lens simulator 180 as if it is placed on the corneal plane 16 at cornea 15.

In a preferred embodiment, the corneal conjugated plane 16" has the same distance to the last turning mirror 105 as does the corneal plane 16. This way, any acuity chart placed in front of the refraction system 100 appears to the subject eye 10 at its real physical distance. For instance, when an acuity chart 190 placed 40 cm away from the eye 10 for near visual acuity test, it does appear 40 cm away. Consequently, the refraction system 100 provides an optical equivalence for testing optical performance of a contact lens simulator 180 as if a contact lens is placed on the cornea 15.

In a preferred embodiment, a cylinder corrector 150 is inserted at the first corneal conjugated plane 16' to correct cylindrical errors of the subject eye 10. The cylinder corrector 150 may consist of a set of cylindrical lenses on a rotatable wheel or a pair of positive and negative lenses rotatable with respect to each other. Also, the cylinder corrector 150 is preferably motorized via a control unit 155 and rotated along 156 and normal to viewing path 13. The construction and control of a cylinder corrector 150 is well known to those skilled in the art.

A viewing path indicator 170 is positioned along the straight viewing path 11 for the eye 10 to align with the straight viewing path 11. The indicator 170 can be formed with a visible LED. The indicator 170 may have different color for the left viewing unit 200 and for the right viewing unit 100 such that easy judgment can be made whether both eyes are aligned with their corresponding viewing paths 21 and 11.

A probe beam generator 130 injects a probe beam 131 via a polarized beam splitter 132 into the viewing path 12 and then into the eye 10. Scattered light of the probe beam 131 from the retina of subject eye 10 is relayed via the pair of optical trombone 115-116 and directed via a dichromic mirror 141 into a refractor sensor 140, which measures refraction errors of the eye 10. The measurement outcome from the refractor sensor 140 is used to drive the translation stage 120 via the moving mechanism 121 to correct defocus error of the eye 10. The measurement outcome from the refractor sensor 140 is also used to drive the cylinder corrector 150 to correct cylindrical error of the eye 10. The moving mechanism 121 can be adjusted manually or with a motorized mechanism. Also, the cylinder corrector 150 can be adjusted manually or with a motorized mechanism via control unit 155.

The defocus error, i.e., the sphere power, of the eye 10 can thus be compensated by the pair of optical trombone 115-116 via adjusting the translation stage 120 with the moving mechanism 121. This way, there is no need to flip trial lenses as does a phoropter or auto-phoropter. Also the moving mechanism 121 can be adjusted manually by patient himself or by an operator. Subjective refinement of defocus correction can thus be obtained with the feedback from the patient. The final position of the translation stage 120 is a measure of the defocus correction needed for compensating the defocus error of the subject eye 10. Similarly, the rotation angle of the cylinder corrector 150 is a measure of the cylinder correction needed for compensating the astigmatism of the subject eye 10. When a best corrected visual acuity is obtained for the eye 10 looking through the viewing unit 100, the position readings of the translation stage 120 and the cylinder corrector 150 can be used to determine the prescription of the eye 10 for eyeglasses or contact lenses.

A viewing path blocker 160 is positioned along the beam path 12 to block or unblock the eye 10 from looking through the viewing unit 100. With the viewing path blocker 160, one eye can be measured naturally without the influence from the other eye.

The refractor sensor 140 can be a wavefront sensor, such as a Hartmann-Shack sensor or a Moiré sensor. The refractor sensor 140 measures refraction errors of the eye 10 through the optical relay, e.g., the pair of optical trombones 115-116. When the pair of optical trombones 115-116 is adjusted to compensate for the eye defocusing, the refractor sensor 140 may be used to measure the residual aberrations between the eye aberrations and the defocusing compensation.

The pair of optical trombones 115-116 is simply a preferred embodiment of an optical relay that provide defocus compensation and unit magnification. The optical relay 115-116 of unit magnification also introduces a conjugated plane 16" of the eye 10 and enables contact lens simulator 180 to place at a plane optically equivalent to that of contact lenses.

To mimic the viewing experience of a phoropter or an auto-phoropter, the viewing path 14 is preferably collinear with the viewing path 11, and the distance between the first turning mirror 102 and the last turning mirror 105 is preferably 100 mm or shorter. The acuity chart 190 is preferably positioned 20 feet (6 meters) away from the eye 10 for distance visual acuity test, and 40 cm away for near visual acuity test.

Preferably, the viewing distance to the acuity chart 190 from the eye 10 is equal to that from the conjugated plane 16". This way the acuity chart 190 appears to the eye 10 equivalent to direct viewing from viewing path 14 through viewing path 11.

Figure 3:
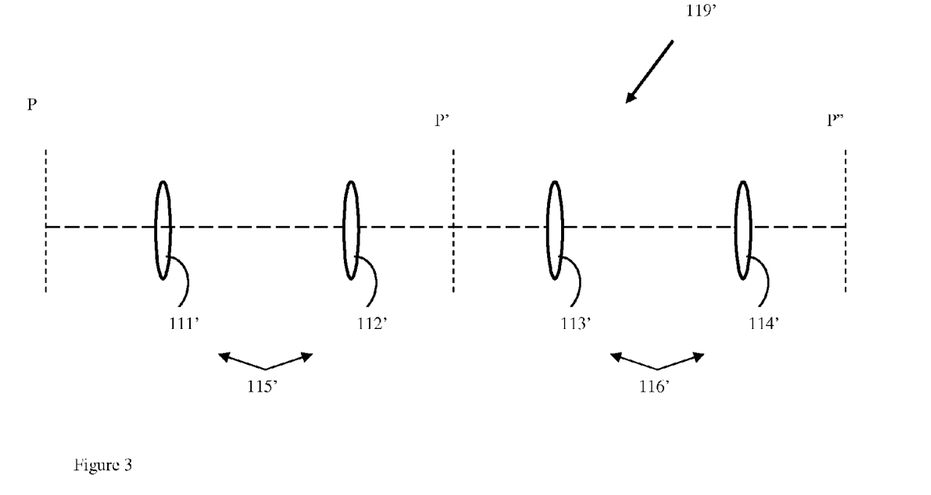
FIG. 3 shows schematically an optical relay of unit magnification and its various modifications.

FIG. 3 shows an optical relay 119' of unit magnification, as a preferred embodiment of the present invention. Preferably, the two relay stages 115'-116' are a pair of optical trombones that collectively produces a unit optical relay. The lenses 111'-114' can be identical in focal length f. Pupil plane P is one focal length f away from the first lens 111'. The distance between lenses 112' and 113' is fixed to twice the focal length, 2f. Conjugated plane P" locates one focal length f away from the last lens 114'. Conjugated plane P" has a unit magnification, i.e., +1 magnification, with respect to the pupil plane P. Optical power of the optical relay 119' varies with the separation between lenses 111'-112' and the separation between lenses 113'-114'.

Figure 3A:
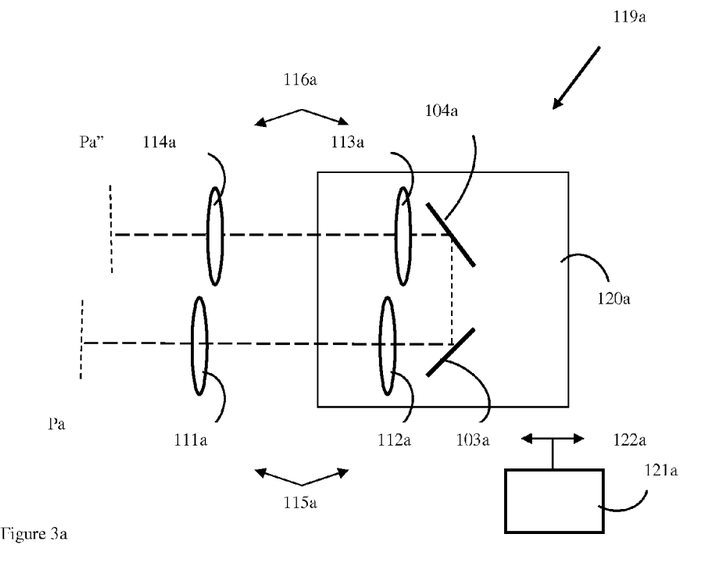
FIG. 3a shows an optical relay of unit magnification consisting of a pair of folded optical trombones.

FIG. 3a shows an optical relay 119a of unit magnification consisting of a pair of folded optical trombones 115a and 116a. Turning mirrors 103a-104a and lenses 112a-113a are mounted on a translation stage 120a. As a pair of optical trombones, the separation between lenses 111a-112a and the separation between lenses 113a-114a can be adjusted simultaneously with a moving mechanism 121a. Consequently, optical power of the optical relay 119a can be adjusted with the translation stage 120a, via a moving mechanism 121a along moving direction 122a.

Figure 3B:
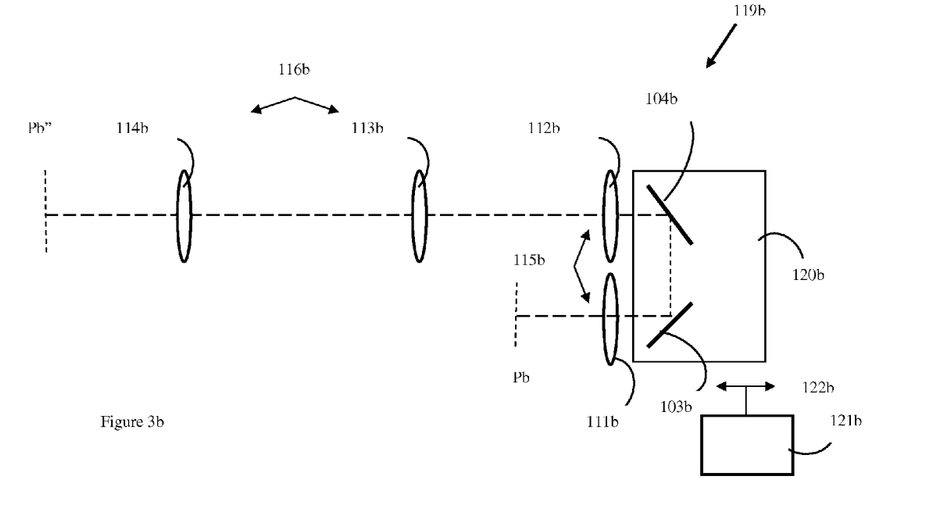
FIG. 3b shows another optical relay of unit magnification in a configuration consisting of an optical trombone and an afocal.

FIG. 3b shows another optical relay 119b of unit magnification, in a configuration consisting of an optical trombone 115b and an afocal 116b. The lenses 111b-114b can also be identically in focal length. Turning mirrors 103b-104b are mounted on a translation stage 120b. In such a configuration, the optical separation between lenses 111b-112b is adjustable with a moving mechanism 121b along moving direction 122b, while the separation between lenses 113b-114b remains constant and is twice of the focal length.

Figure 3C:
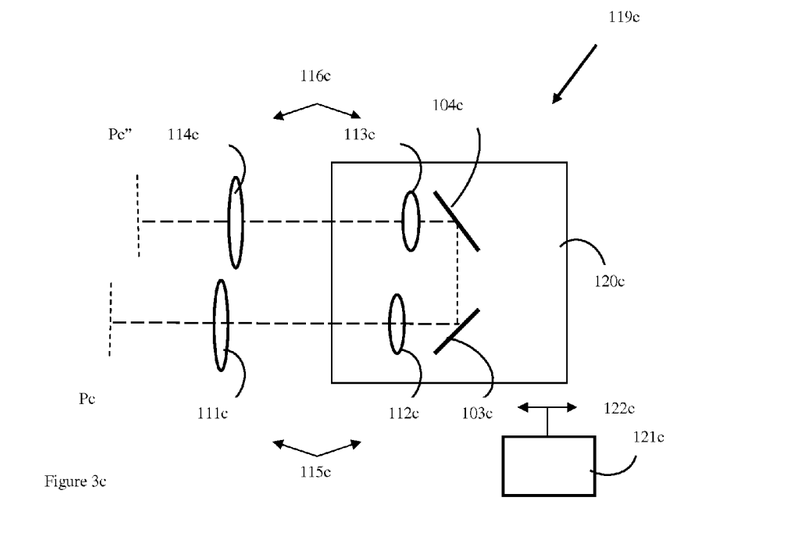
FIG. 3c shows further another optical relay of unit magnification in a configuration consisting of a pair of complement optical relay.

FIG. 3c shows further another optical relay 119c of unit magnification, in a configuration consisting of a pair of complement optical relay 115c and 116c. In an embodiment, lenses 112c-113c are identical with a focal length f1, and lenses 111c and 114c are identical but with a different focal length f2. That is, the optical relay 115c has a magnification of x and the other optical relay 116c has a magnification of 1/x.

Turning mirrors 103c-104c and lenses 112c-113c are mounted on a translation stage 120c. To introduce a defocus power correction, the separation between lenses 111c-112c and the separation between lenses 113c-114c can be adjusted simultaneously with a moving mechanism 121c along moving direction 122c.

Figure 3D:
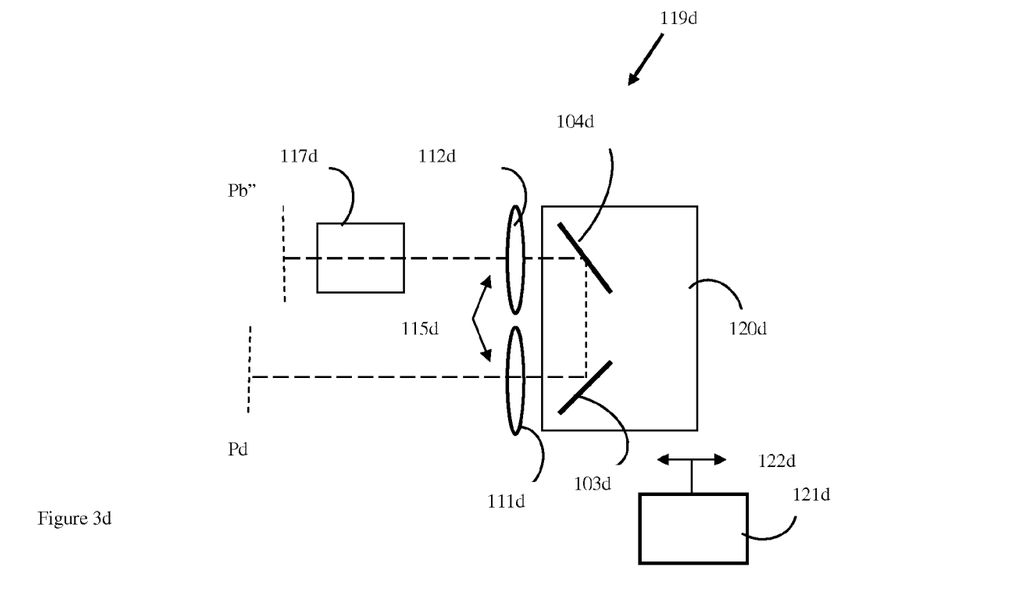
FIG. 3d shows further another optical relay of unit magnification in a configuration consisting of an optical trombone and an image-reversing prism.

FIG. 3d shows further another optical relay 119d of unit magnification, in a configuration consisting of an optical trombone 115d and an image-reversing prism 117d. The image-reversing prism 117d can be made of a pair of Porro prisms placed at right angles to each other such that the image is rotated and reversed. Porro prism is well known to those skilled in the art.

Turning mirrors 103d-104d are mounted on a translation stage 120d. In such a configuration, the optical separation between lenses 111d-112d is adjustable with a moving mechanism 121d along moving direction 122d.

Figure 4:
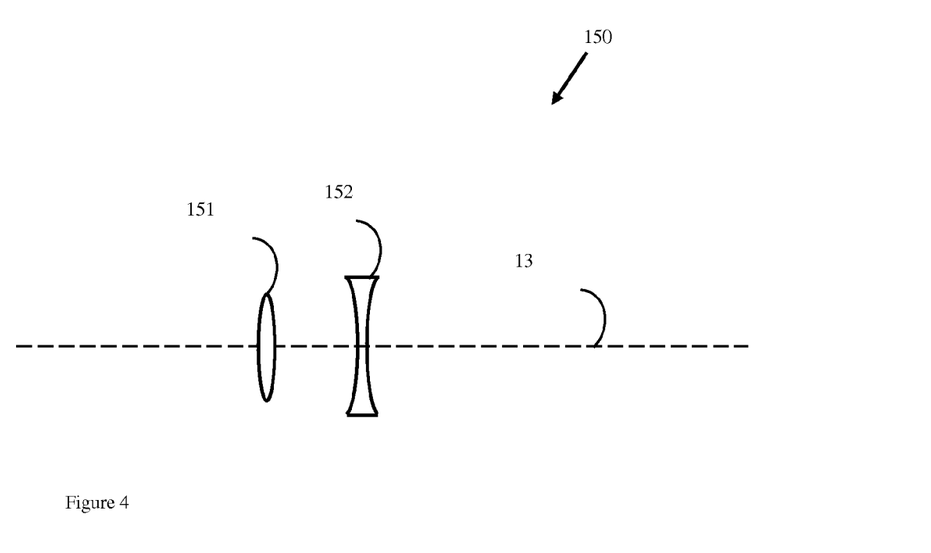
FIG. 4 shows schematically a pair of positive and negative cylinder lenses that produces an effective cylindrical lens of adjustable power and axis.

FIG. 4 shows a pair of positive 151 and negative 152 cylinder lenses that produces an effective cylindrical lens of adjustable power and axis. The paired cylinder lenses 151-152 forms a cylinder corrector 150. The positive cylinder lens 151 and negative cylinder lens 152 can be rotated around the viewing path 12 independently to adjust cylinder power and axis. The construction and operation of a cylinder corrector 150 with paired positive 151 and negative 152 cylindrical lenses is well known to those skilled in the art.

As shown in FIG. 3 and FIGS. 3a)-3d), defocus power correction with an optical relay can be made continuously. Lab experiments have demonstrated that, with instrumentation conditions, defocus power correction with an optical relay can be made and measured to an accuracy better than 0.125 D and to a precision better than 0.06 D. Also as shown in FIG. 4, cylinder power correction and axis adjustment can be made continuously. Lab experiments have also demonstrated that, with instrumentation conditions, cylindrical power correction with a pair of positive and negative lenses can be made and measured to an accuracy better than 0.125 D and to a precision better than 0.06 D. As a result, the refraction system 300 is capable to provide refraction measurements and prescription substantially more accurate and more precise than the industrial standard with a phoropter or autophoropter, i.e., 0.25 D in sphere and cylinder power and 1 degree in cylinder axis.

Besides, the refractor sensor 140 of the refraction system 300 is preferably a wavefront sensor, such as a Hartmann-Shack wavefront sensor or a Moire wavefront sensor. As a result, the refraction system 300 is capable to provide measurement data of wavefront aberrations.

Consequently, refraction system 300 is capable to perform objective and subjective visual acuity test, to provide precise prescription, and to measure wavefront aberrations. On the other hand, the precise prescription can be rounded off and converted to a precision of the industrial standard, i.e., 0.25 D in sphere and cylinder power and 1 degree in cylinder axis.

Therefore, in a preferred embodiment, refraction system 300 is used to provide prescription of standard precision for conventional eyeglasses and contact lenses. In another preferred embodiment, refraction system 300 is used to provide high precision prescription for custom or premium eyeglasses and contact lenses. In further another preferred embodiment, refraction system 300 has a first software algorithm to provide a first prescription of standard precision for conventional eyeglasses and contact lenses and a second software algorithm to provide a second prescription of high precision for fabricating custom or premium eyeglasses and contact lenses. The second prescription of high precision is preferably to provide in a non-conventional format and is coded and used for a specific lens fabrication process.

Figure 5:
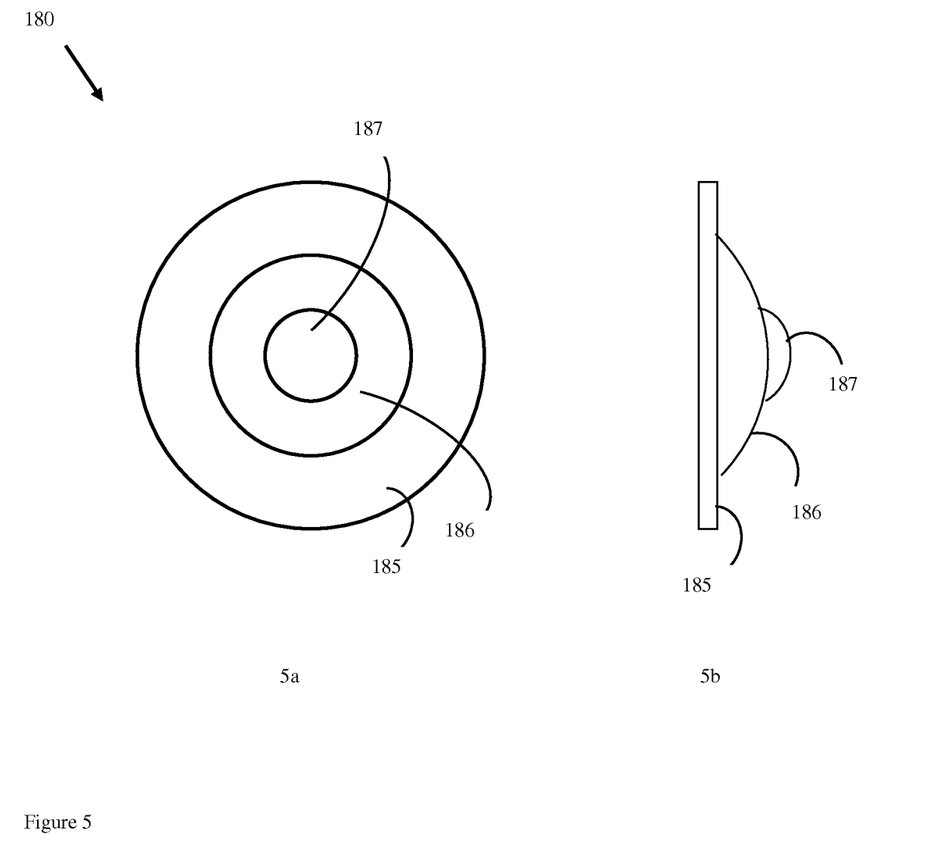
FIG. 5 shows schematically a contact lens simulator or phase plate for a bi-focal lens to be inserted at a corneal conjugated plane, in accordance with the present invention.

FIG. 5 shows schematically a contact lens simulator or phase plate 180 for a bi-focal lens to be inserted at a corneal conjugated plane 16″, in accordance with the present invention. The bi-focal lens, i.e., a most simple form of multifocal lens, consists of typically three concentric optical zones: a periphery zone 185, a base power zone 186, and an added power zone 187. The base power zone 186 may have an outer diameter of about 6 mm and the added power zone 187 of about 2 mm. For presbyopia correction, the added power is typically range from +1.25 D to +3 D. A contact lens simulator or phase plate 180 is commonly made of PMMA or other contact lens materials and has optical characterizations of the multifocal contact lens that is to simulate.

Figure 6:
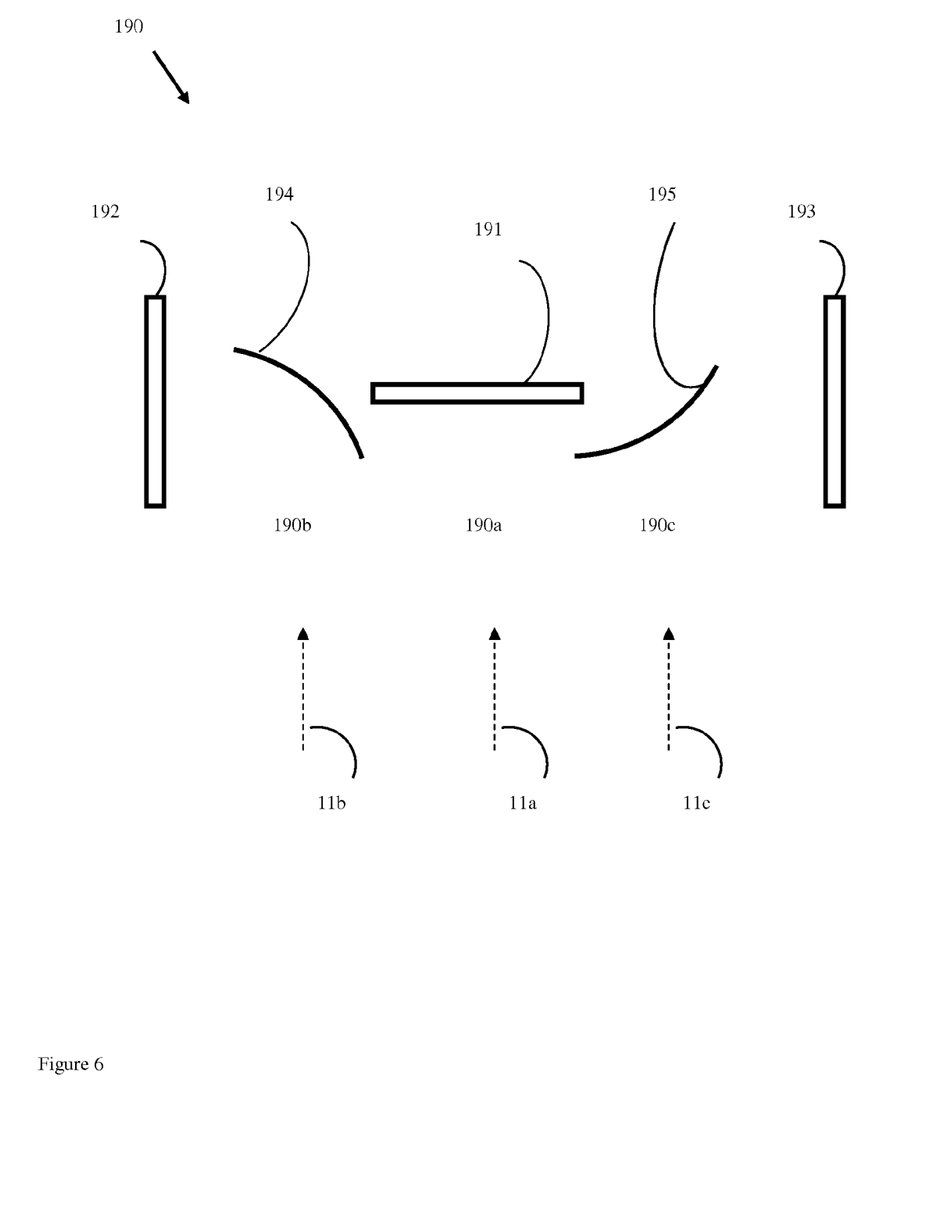
FIG. 6 shows schematically a multiple vergence acuity chart, in accordance with the present invention.

FIG. 6 shows schematically a multiple vergence acuity chart 190, in accordance with the present invention. The acuity chart 190 consists of three sections, e.g. the central 190a, the left 190b and the right 190c sections. In the central section 190a, the viewing path 11a looks at the central acuity chart 191 directly. In the left section 190b, the viewing path 11b looks at the left acuity chart 192 via a negative reflector 194. In the right section 190c, the viewing path 11c looks at the right acuity chart 193 via a positive reflector 195. The negative reflector 194 introduces a negative vergence to the eye 10, i.e., producing a virtual image close to the subject eye 10. The positive reflector 195 introduces a positive vergence to the subject eye 10, i.e., producing a virtual image further away from the eye 10. The three sections provide, for instance, OD, −0.25 D and +0.25 D vergence, respectively. The three sections extend preferably 3 to 5 degrees in the field of view. This way, the subject eye 10 can look at the three sections 190a-190c simultaneously and compare the best acuity among the three acuity charts 191-193. The best corrected visual acuity (BCVA) shall correspond to a best visual acuity resolvable at the OD section.

Figure 7:
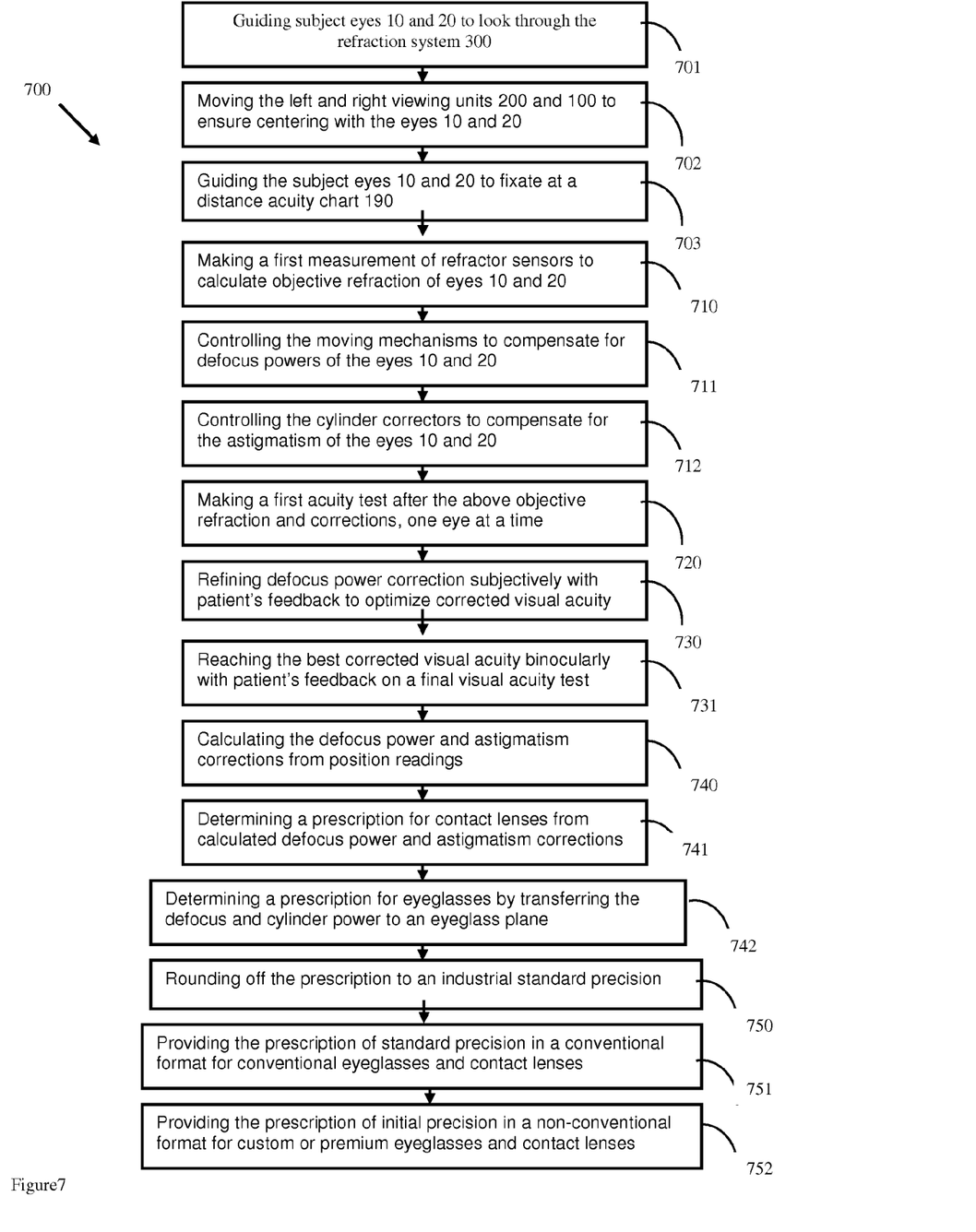
FIG. 7 shows schematically an operation procedure to provide prescription for eyeglasses and contact lenses, in accordance with the present invention.

FIG. 7 shows in a block diagram of an operation procedure 700 to provide prescription for eyeglasses and contact lenses, in accordance with the present invention. Referring to FIGS. 1, 2 and 7, the operation procedure 700 comprises the following steps:

701) Guiding subject eyes 10 and 20 to look through the refraction system 300;

702) Moving the left and right viewing units 200 and 100 to ensure centering with the eyes 10 and 20, such that the right eye 10 can see the right viewing path indicator 170, and the left eye 20 can see the left viewing path indicator;

703) Guiding the subject eyes 10 and 20 to fixate at a distance acuity chart 190;

710) Making a first measurement of refractor sensors to calculate objective refraction of eyes 10 and 20, i.e., the right refractor sensor 140 measures the refractive errors of the right eye 10, and the left refractor sensor measures the left eye 20;

711) Controlling the moving mechanisms to compensate for defocus powers of the eyes 10 and 20, i.e., the right moving mechanism 121 corrects defocus power of the right eye 10, and the left moving mechanism corrects for the left eye 20;

712) Controlling the cylinder correctors to compensate for the astigmatism of the eyes 10 and 20, i.e., the right cylinder corrector 150 corrects the astigmatism for the right eye 10, and the left cylinder corrector corrects for the left eye 20;

720) Making a first visual acuity test after the above objective refraction and corrections, one eye at a time, e.g. test the right eye 10 while the right viewing path blocker 160 is open and the left viewing path blocker is closed, and then the left and right are reversed;

730) Refining defocus power correction subjectively with patient's feedback to optimize the corrected visual acuity, one eye at a time, e.g., the right moving mechanism 121 is adjusted according to the patient's judgment through the right viewing unit 100, and then the left moving mechanism is adjusted through the left viewing unit 200;

731) Reaching the best corrected visual acuity subjectively and binocularly with patient's feedback on a final visual acuity test, e.g., the defocus power corrections are fine tuned for optimal visual acuity while both viewing paths are open;

740) Calculating the defocus power and astigmatism corrections from position readings of the translation stages and the cylinder correctors, with reference to corneal planes of the eyes 10 and 20, respectively;

741) Determining a prescription for contact lenses from calculated defocus power and astigmatism corrections, i.e., the prescription for OD is referred to a right corneal plane 16 and the prescription for OD is referred to a left corneal plane;

742) Determining a prescription for eyeglasses by transferring the defocus and cylinder power to an eyeglass plane and by adding a pupil distance between the eyes 10 and 20;

750) Rounding off the prescription to an industrial standard precision, e.g., 0.25 D for defocus and cylinder power, and 1 degree for cylinder axis;

751) Providing the prescription of standard precision in a conventional format for conventional eyeglasses and contact lenses;

752) Providing the prescription of initial precision in a non-conventional format for fabricating custom or premium eyeglasses and contact lenses.

By this way, the operation procedure 700 provides a prescription for contact lenses, with measurement references to subject right corneal plane 16 and left corneal plane, respectively. The operation procedure 700 also provides a prescription for eyeglasses, with a calculated reference to an eyeglass plane, which typically takes a nominal distance of 12 mm from a corneal plane. To match the industrial standard, a software algorithm associated with step 750 rounds off the initial prescriptions to a standard precision of 0.25 D for sphere and cylinder power and 1 degree fro cylinder axis. The operation procedure 700 can thus employ the refraction system 300 to provide a standard prescription of standard precision.

In a preferred embodiment, a software algorithm associated with step 752 presents the initial prescription of high precision in a different, non-conventional format for fabricating custom or premium eyeglasses or contact lenses. Any software algorithm associated with the operation procedure 700 is preferably implemented into the refraction system 300. The refraction system 300 is thus capable to provide a prescription with precision higher than conventional standard and to meet requirements for fabricating custom or premium eyeglasses and contact lenses.

Figure 8:
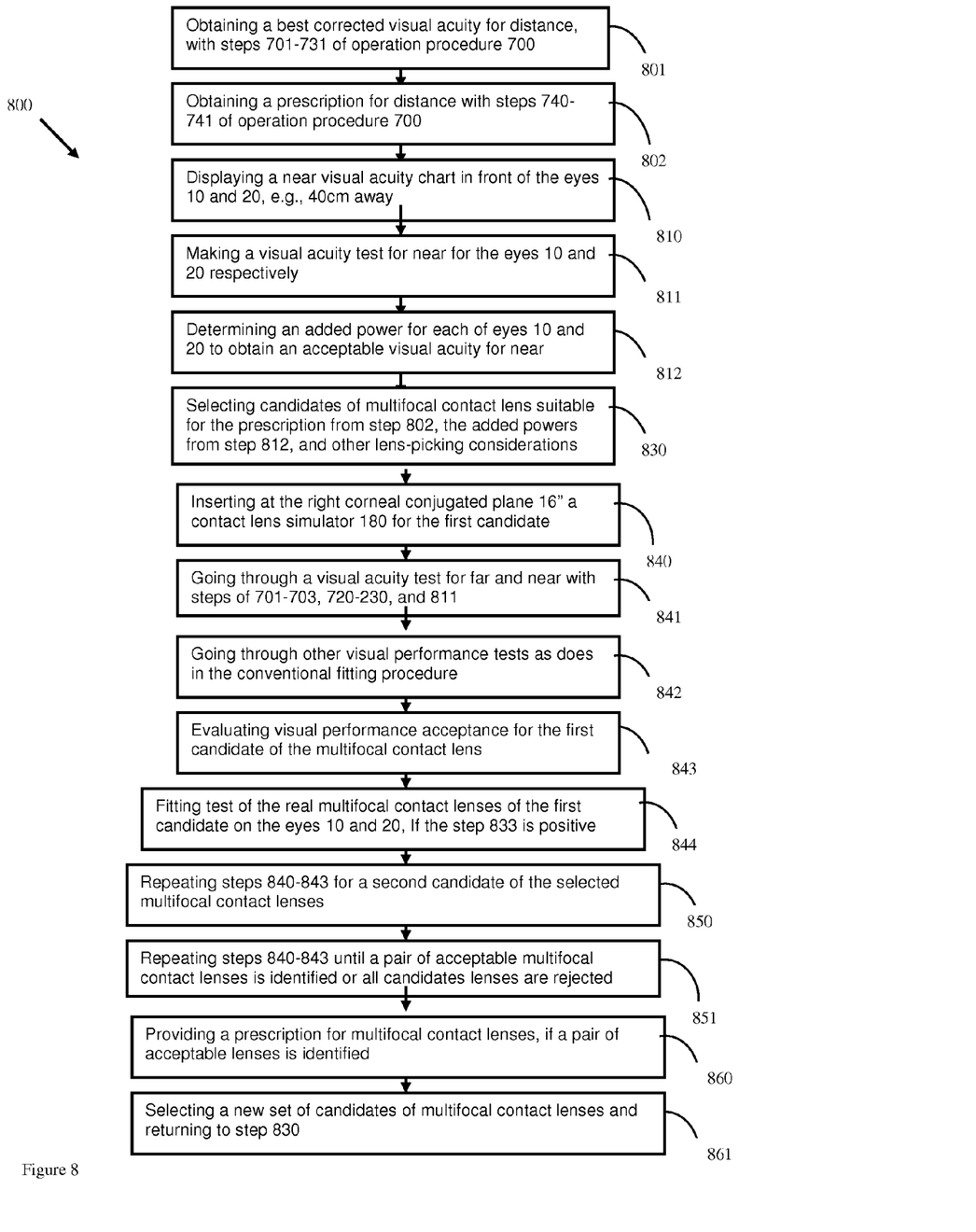
FIG. 8 shows schematically an operation procedure to facilitate multi-focus contact lens fitting, in accordance with the present invention.

FIG. 8 shows a block diagram of an operation procedure 800 to facilitate multifocal contact lens fitting, in accordance with the present invention. Referring to FIGS. 1, 2, 7 and 8, the operation procedure 800 comprises the following steps:

801) Obtaining a best corrected visual acuity for distance, with steps 701-731 of operation procedure 700;

802) Obtaining a prescription for distance with steps 740-741 of operation procedure 700;

810) Displaying a near visual acuity chart in front of the eyes 10 and 20, e.g., 40 cm away;

811) Making a visual acuity test for near for the eyes 10 and 20 respectively, without changing the defocus and cylinder power corrections;

812) Determining an added power for each of eyes 10 and 20 to obtain an acceptable visual acuity for near, via adjusting the right translation stage 120 and the left translation stage;

830) Selecting candidates of multifocal contact lens suitable for the prescription from step 802, the added powers from step 812, and other lens-fitting considerations;

840) Inserting at the right corneal conjugated plane 16" a contact lens simulator 180 for the first candidate of selected multifocal contact lenses, and doing the same for the left unit 200;

841) Going through a visual acuity test for far and near with steps of 701-703, 720-230, and 811, 842) Going through other visual performance tests as does in the conventional fitting procedure, e.g., ghost image test, binocular tests of added power offset and balance, intermediate visual acuity test.

843) Evaluating visual performance acceptance for the first candidate of the multifocal contact lens;

844) Fitting test of the real multifocal contact lenses of the first candidate on the eyes 10 and 20, If the outcome of step 843 is positive;

850) Repeating steps 840-843 for a second candidate of the selected multifocal contact lenses, if the outcome of step 843 is negative;

851) Repeating steps 840-843 until a pair of acceptable multifocal contact lenses is identified or all the candidates of selected multifocal contact lenses are rejected;

860) Providing a prescription for multifocal contact lenses, if a pair of acceptable lenses is identified;

861) Selecting a new set of candidates of multifocal contact lenses and returning to step 830.

By this way, the operation procedure 800 makes effective use of contact lens simulator 180 together with the refraction system 100 to facilitate multifocal contact lens fitting for presbyopia correction. A poor candidate of multifocal contact lens can be identified and rejected via steps 840-843, without a need to insert into the eyes 10 and 20. Thus, the operation procedure 800 provides an effective screen test of the candidates of selected multifocal contact lenses and an effective simulation of the patient's adaptation of multifocal contact lenses. Consequently, the operation procedure 800 can expedite the test process for each lens candidate, reduce the number of lenses to put on the eyes, and refine prescription with power adjustment available in the refraction system 300.

The present invention is related to a refraction system combining the advantages of an objective auto-refractor and a subjective auto-phoropter via use of optical trombones to provide defocus power corrections and to implement refraction measurement along an open field viewing path. The present invention of continuation in part is related to a refraction system facilitating contact lens fitting with insertion of contact lens simulator or phase plate at a corneal conjugated plane and with direct measurement of refraction errors referring to the corneal plane. Although aspects of the present invention are described with specific embodiments, various modifications can be made without departing from the scopes of the appended claims.

What is claimed is:

1. A refraction system for facilitating multifocal contact lens fitting for left and right subject eyes, comprising:
    a first optical relay of unit magnification defining a first viewing path, a first working plane, and a conjugated plane of said first working plane;
    a second optical relay of unit magnification defining a second viewing path, a second working plane, and a conjugated plane of said second working plane;
    a first contact lens simulator insertable at said conjugated plane of said first working plane;
    a second contact lens simulator insertable at said conjugated plane of said second working plane; and
    a moving mechanism coupled to translate said first viewing path with respect to said second viewing path;
    wherein said first and second contact lens simulators are optically equivalent to place on said first and second working planes, and wherein said first viewing path and said second viewing path are directed toward an external acuity chart.

2. The refraction system of claim 1, wherein said first optical relay and said second optical relay include each a pair of optical trombones.

3. The refraction system of claim 1, wherein said first optical relay and said second optical relay include each an optical trombone and an afocal relay.

4. The refraction system of claim 1, wherein said first optical relay and said second optical relay include each a pair of optical trombone with complementary magnifications.

5. The refraction system of claim 1, wherein said first optical relay and said second optical relay include each a moving mechanism for defocus power adjustments.

6. The refraction system of claim 1, wherein said first and second viewing paths enable apparently straight and direct viewing toward said external acuity chart.

7. The refraction system of claim 1, wherein said first and second viewing paths include each a viewing path indicator.

8. The refraction system of claim 1, wherein said first and second viewing paths include each a refractor sensor.

9. The refraction system of claim 1, wherein said first and second viewing paths include each a cylinder corrector.

10. The refraction system of claim 1, wherein s said first and second viewing paths include each a viewing path stop.

11. The refraction system of claim 1, wherein said first working plan and said conjugated plane of said first working plane have the same distance to said external acuity chart.

12. The refraction system of claim 1, wherein said second working plan and said conjugated plane of said second working plane have the same distance to said external acuity chart.

13. The refraction system of claim 1, wherein said first and second contact lens simulators have each an optical character of a multifocal contact lens.

14. The refraction system of claim 1, wherein said external acuity chart is a multi-vergence acuity chart.

15. The refraction system of claim 1, further comprising:
    a system processor including a first software algorithm to provide a first prescription of standard precision for conventional eyeglasses and contact lenses and a second software algorithm to provide a second prescription of high precision in a non-conventional format for fabricating custom or premium eyeglasses and contact lenses.

16. A method for facilitating multifocal contact lens fitting for left and right subject eyes, comprising the steps of:
    providing a first optical relay of unit magnification to define a first viewing path, a first working plane, and a conjugated plane of said first working plane;
    providing a second optical relay of unit magnification to define a second viewing path, a second working plane, and a conjugated plane of said second working plane;
    inserting a first contact lens simulator at said conjugated plane of said first working plane;
    inserting a second contact lens simulator at said conjugated plane of said second working plane;
    providing a moving mechanism coupled to translate said first viewing path with respect to said second viewing path
    and
    positioning an acuity chart at a predetermined distance away from said first and second optical relays;
    wherein said first and second contact lens simulators are placed on optically equivalent to said first and second working planes when viewing through said first and second viewing paths.

17. The method of claim 16, further comprising the steps of:
    providing a first refractor sensor capable of measuring first refractive errors along said first viewing path; and
    providing a second refractor sensor capable of measuring second refractive errors along said second viewing path;
    wherein said first and second refractor sensors are capable to provide objective measurement of refraction errors of said left and right subject eyes.

18. The method of claim 16, further comprising the steps of:
    providing a first moving mechanism capable of adjusting first defocus power along said first viewing path; and
    providing a second moving mechanism capable of adjusting second defocus power along said second viewing path;
    providing a first cylinder corrector capable of adjusting first cylinder power and axis in said first viewing path; and
    providing a second cylinder corrector capable of adjusting second cylinder power and axis in said second viewing path;
    wherein said first and second moving mechanisms are capable to compensate for refraction errors of said left and right subject eyes, and wherein said first and second cylinder correctors are capable to compensate for cylindrical errors of said left and right subject eyes.

19. The method of claim 16, further comprising the steps of:
  providing a system processor including a first software algorithm to provide a first prescription of standard precision for conventional eyeglasses and contact lenses and a second software algorithm to provide a second prescription of high precision in a non-conventional format for fabricating custom or premium eyeglasses and contact lenses.

20. A refraction system for facilitating multifocal contact lens fitting for left and right subject eyes, comprising:
  a first optical relay of unit magnification defining a first viewing path, a first working plane, and a conjugated plane of said first working plane;
  a second optical relay of unit magnification defining a second viewing path, a second working plane, and a conjugated plane of said second working plane;
  a first contact lens simulator insertable at said conjugated plane of said first working plane;
  a second contact lens simulator insertable at said conjugated plane of said second working plane;
  a first refractor sensor capable of measuring first refractive errors along said first viewing path;
  a second refractor sensor capable of measuring second refractive errors along said second viewing path;
  a first moving mechanism capable of adjusting first defocus power along said first viewing path;
  a second moving mechanism capable of adjusting second defocus power along said second viewing path;
  a first cylinder corrector capable of adjusting first cylinder power and axis in said first viewing path;
  a second cylinder corrector capable of adjusting second cylinder power and axis in said second viewing path; and
  a moving mechanism coupled to translate said first viewing path with respect to said second viewing path;
  wherein said first and second contact lens simulators are optically equivalent to place on said first and second working planes, and wherein said first viewing path and said second viewing path are directed toward an external acuity chart.

* * * * *